(12) United States Patent
Smith et al.

(10) Patent No.: US 9,194,829 B2
(45) Date of Patent: Nov. 24, 2015

(54) PROCESS FOR PERFORMING AUTOMATED MINERALOGY

(71) Applicant: FEI Company, Hillsboro, OR (US)

(72) Inventors: Michael D. Smith, New Farm (AU); Kurt Moeller, Kenmore (AU)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/730,358

(22) Filed: Dec. 28, 2012

(65) Prior Publication Data

US 2014/0183357 A1    Jul. 3, 2014

(51) Int. Cl.
| | |
|---|---|
| H01J 37/20 | (2006.01) |
| H01J 37/21 | (2006.01) |
| G01N 23/22 | (2006.01) |
| G01N 23/225 | (2006.01) |

(52) U.S. Cl.
CPC ............ *G01N 23/2252* (2013.01); *H01J 37/20* (2013.01); *H01J 37/21* (2013.01)

(58) Field of Classification Search
CPC .... H01J 37/20; H01J 37/21; H01J 2237/2448
See application file for complete search history.

(56) References Cited

U.S. PATENT DOCUMENTS

| | | | | |
|---|---|---|---|---|
| 3,519,824 | A | * | 7/1970 | Weinstock et al. ........ 250/358.1 |
| 4,037,101 | A | | 7/1977 | Okumura et al. |
| 4,136,429 | A | | 1/1979 | Brandes |
| 4,242,586 | A | | 12/1980 | Warble |
| 4,435,507 | A | | 3/1984 | Stenkvist |
| 4,476,386 | A | | 10/1984 | Reid et al. |
| 4,587,424 | A | | 5/1986 | Grau |
| 4,592,082 | A | | 5/1986 | Pawloski |
| 4,807,148 | A | | 2/1989 | Lacey |

(Continued)

FOREIGN PATENT DOCUMENTS

| | | |
|---|---|---|
| CN | 100498309 | 6/2009 |
| JP | 05087707 | 4/1993 |

(Continued)

OTHER PUBLICATIONS

Figueroa et al., "Advanced Discrimination of Hematite and Magnetite by Automated Mineralogy", Proceedings of 10th Int'l Congress for Applied Mineralogy (ICAM), Aug. 1-5, 2011.*

(Continued)

*Primary Examiner* — Nicole Ippolito
*Assistant Examiner* — James Choi
(74) *Attorney, Agent, or Firm* — Scheinberg & Associates, PC; Michael O. Scheinberg; John E. Hillert (57) ABSTRACT

A method and system for determining the mineral content of a sample using an electron microscope. The method includes directing an electron beam toward an area of interest of a sample, the area of interest comprising an unknown composition of minerals. The working distance between the backscattered electron detector of the microscope and the area of interest of the sample is determined. Compensation is made for the difference between the working distance and a predetermined working distance in which the predetermined working distance being the working distance that provides desired grayscale values for detected backscattered electrons. One way of compensating for working distance variation is to used an autofocus feature of the microscope to adjust the working distance. Backscattered electrons from the area of interest of the sample are then detected.

19 Claims, 7 Drawing Sheets

(56) References Cited

U.S. PATENT DOCUMENTS

| | | | |
|---|---|---|---|
| 4,834,943 A | 5/1989 | Yoshiyama | |
| 4,839,516 A | 6/1989 | Freeman et al. | |
| 5,084,618 A | 1/1992 | Ito | |
| 5,555,198 A | 9/1996 | Asano | |
| RE35,514 E | 5/1997 | Albrecht et al. | |
| 5,741,707 A | 4/1998 | Herron et al. | |
| 5,798,525 A | 8/1998 | Benizri-Carl et al. | |
| 5,841,149 A | 11/1998 | Spink et al. | |
| 5,866,903 A | 2/1999 | Morita et al. | |
| 5,906,919 A | 5/1999 | Garini et al. | |
| 5,991,028 A | 11/1999 | Cabib et al. | |
| 6,018,587 A | 1/2000 | Cabib | |
| 6,066,459 A | 5/2000 | Garini et al. | |
| 6,072,178 A | 6/2000 | Mizuno | |
| 6,093,930 A | 7/2000 | Boyette, Jr. et al. | |
| 6,122,343 A | 9/2000 | Pidcock | |
| 6,140,643 A | 10/2000 | Brown et al. | |
| 6,166,380 A | 12/2000 | Kitagawa et al. | |
| 6,282,301 B1 | 8/2001 | Haskett | |
| 6,341,257 B1 | 1/2002 | Haaland | |
| 6,377,652 B1 | 4/2002 | Sturm | |
| 6,466,929 B1 | 10/2002 | Brown et al. | |
| 6,470,335 B1 | 10/2002 | Marusak | |
| 6,584,413 B1 | 6/2003 | Keenan et al. | |
| 6,658,143 B2 | 12/2003 | Hansen et al. | |
| 6,674,894 B1 | 1/2004 | Parker et al. | |
| 6,687,620 B1 | 2/2004 | Haaland et al. | |
| 6,711,503 B2 | 3/2004 | Haaland | |
| 6,723,871 B2 | 4/2004 | Tada et al. | |
| 6,724,940 B1 | 4/2004 | Qian et al. | |
| 6,765,205 B2 | 7/2004 | Ochiai et al. | |
| 6,842,702 B2 | 1/2005 | Haaland et al. | |
| 6,888,920 B2 | 5/2005 | Blank et al. | |
| 6,977,723 B2 | 12/2005 | Lemmo et al. | |
| 6,993,170 B2 | 1/2006 | Johnson et al. | |
| 7,053,365 B2 | 5/2006 | Shimomura | |
| 7,061,605 B2 | 6/2006 | Lemmo et al. | |
| 7,108,970 B2 | 9/2006 | Levinson | |
| 7,132,652 B1 | 11/2006 | Testoni | |
| 7,139,415 B2 | 11/2006 | Finkbeiner | |
| 7,161,672 B2 | 1/2007 | Gornushkin et al. | |
| 7,243,030 B2 | 7/2007 | Reeve et al. | |
| 7,400,770 B2 | 7/2008 | Keaton et al. | |
| 7,436,510 B2 | 10/2008 | Grun et al. | |
| 7,490,009 B2 | 2/2009 | Gottlieb et al. | |
| 7,790,465 B2 | 9/2010 | Otvos | |
| 7,804,059 B2 | 9/2010 | Harrison | |
| 7,930,106 B2 | 4/2011 | Carrick | |
| 7,979,217 B2 | 7/2011 | Gottlieb et al. | |
| 8,060,173 B2 | 11/2011 | Goode, Jr. et al. | |
| 8,119,991 B2 | 2/2012 | Harrison | |
| 2002/0102102 A1* | 8/2002 | Watanabe et al. | 396/89 |
| 2002/0169589 A1 | 11/2002 | Banki et al. | |
| 2003/0136907 A1* | 7/2003 | Takane et al. | 250/310 |
| 2004/0011958 A1 | 1/2004 | Wright et al. | |
| 2004/0027350 A1 | 2/2004 | Kincaid et al. | |
| 2004/0099805 A1 | 5/2004 | Ochiai et al. | |
| 2004/0147830 A1 | 7/2004 | Parker et al. | |
| 2005/0037515 A1 | 2/2005 | Nicholson et al. | |
| 2005/0060868 A1 | 3/2005 | McMurtry | |
| 2005/0165290 A1 | 7/2005 | Kotsianti et al. | |
| 2005/0258366 A1* | 11/2005 | Honda et al. | 250/310 |
| 2006/0043294 A1* | 3/2006 | Yamaguchi et al. | 250/310 |
| 2006/0051251 A1 | 3/2006 | Desrosiers et al. | |
| 2006/0227922 A1* | 10/2006 | Pop et al. | 376/308 |
| 2006/0291619 A1 | 12/2006 | Statham | |
| 2007/0109557 A1* | 5/2007 | Saito et al. | 356/602 |
| 2007/0181793 A1 | 8/2007 | Harrison | |
| 2007/0279629 A1 | 12/2007 | Grun et al. | |
| 2008/0137082 A1 | 6/2008 | Grun et al. | |
| 2008/0250881 A1 | 10/2008 | Dona | |
| 2009/0039261 A1* | 2/2009 | Toyoda et al. | 250/310 |
| 2010/0044566 A1 | 2/2010 | Donitz et al. | |
| 2010/0060893 A1 | 3/2010 | Norton et al. | |
| 2011/0144922 A1 | 6/2011 | Corbett et al. | |
| 2011/0147587 A1* | 6/2011 | Yang et al. | 250/310 |
| 2011/0301869 A1 | 12/2011 | Gottlieb et al. | |
| 2012/0019648 A1* | 1/2012 | Hoshino et al. | 348/80 |
| 2012/0154668 A1* | 6/2012 | Kimura et al. | 348/348 |
| 2012/0314206 A1 | 12/2012 | Spizig et al. | |
| 2013/0015351 A1 | 1/2013 | Kooijman et al. | |
| 2013/0134307 A1 | 5/2013 | Routh, Jr. | |
| 2013/0254948 A1* | 9/2013 | Hartong et al. | 850/1 |

FOREIGN PATENT DOCUMENTS

| | | |
|---|---|---|
| JP | 08015185 | 1/1996 |
| JP | 10312763 | 11/1998 |
| JP | 2000249668 | 9/2000 |
| JP | 2001006597 | 1/2001 |
| JP | 2001066269 | 3/2001 |
| JP | 2002189005 | 7/2002 |
| JP | 2005274352 | 10/2005 |
| JP | 2009-075071 | 4/2009 |
| JP | 2011113640 | 6/2011 |
| RU | 2054660 | 2/1996 |
| WO | 9905503 | 2/1999 |
| WO | 2008013597 | 1/2008 |
| WO | 2009100404 | 8/2009 |

OTHER PUBLICATIONS

Figueroa, German, et al., 'Advanced discrimination of hematite and magnetite by automated mineralogy,' 10th International Congress for Applied Mineralogy, Aug. 1-5, 2011, pp. 197-204.

Miller, Jeff, "Jeff's (Fairly Comprehensive) Raith Usage Notes," Marcus Group, Harvard University, Unknown date Version 20040929.1, 12 pages.

Newbury, Dale E., "Chemical compositional mapping by microbeam analysis at the micrometer scale and finer," Microelectronics Journal, 1997. pp. 489-508, vol. 28.

Newbury, Dale "Pushing the Envelope with SEM/SDD-EDS Mapping: X-ray Spectrum Image Mapping in 30 Seconds or Less, but What are the Real Limits?" Proc. of SPIE, 2010, 9 pages, vol. 7729.

Oversluizen, Tom, et al., "Kinematic mounting systems for National Synchrotron Light Source beamlines and experiments," Rev. Sci. Instrum., Jan. 1992, pp. 1285-1288, vol. 63 No. 1.

Pirrie, Duncan, et al., "Rapid quantitative mineral and phase analysis using automated scanning electron microscopy (QemSCAN); potential applications in forensic geoscience," Forensic Geoscience: Principles, Techniques and Applications, 2004, pp. 123-136.

Pye, Kenneth, et al., "Forensic Geoscience: Principles, Techniques and Applications," The Geological Society, Mar. 3 & 4, 2003, 55 pages.

Slocum, A. H., "Kinematic couplings for precision fixturing—Part I: Formulation of design parameters," Precision Engineering, Apr. 1988, pp. 85-92, vol. 10 No. 2.

Slocum, A. H., et al., "Kinematic couplings for precision fixturing—Part 2: Experimental determination of repeatability and stiffness," Precision Engineering, Jul. 1988, pp. 115-122, vol. 10 No. 3.

Slocum, Alexander H., "Design of three-groove kinematic couplings," Precision Engineering, Apr. 1992, pp. 67-77, vol. 14, No. 2.

Slocum, Alexander, "Kinematic couplings: a review of design principles and applications," International Journal of Machine Tools & Manufacture, 2010, pp. 310-327, vol. 50.

Sutherland, D. N., et al., "Application of Automated Quantitative Mineralogy in Mineral Processing," Minerals Engineering, 1991, pp. 753-762, vol. 4 No. 7-11.

Sutherland, D. N., "Image Analysis for Off-Line Characterisation of Mineral Particles and Prediction of Processing Properties," Part. Part. Syst. Charact., 1993, pp. 271-274, vol. 10.

Unknown, "Raith e_LINE User Guide," online, Nov. 2009,18 pages.

Van Hoek, Corrie J.G., et al., "A SEM-EDS Study of Cultural Heritage Objects with Interpretation of Constituents and Their Distribution Using PARC Data Analysis," Microsc. Microanal. 2011, pp. 656-660, vol. 17.

Zelenika, S., et al., "Kinematic Couplings for Synchrotron Radiation Instrumentation," 2nd International Workshop on Mechanical Engineering Design of Synchrotron Radiation Equipment and Instrumentation, Sep. 5-6, 2002, 9 pages.

(56) References Cited

OTHER PUBLICATIONS

Ashton, Edward A., "Multialgorithm solution for automated multispectral target detection," Opt. Eng., Apr. 1999, pp. 717-724, vol. 38, No. 4.

Benz, Ursula C., et al., "Multi-resolution, object-oriented fuzzy analysis of remote sensing data for GIS-ready information," ISPRS Journal of Photogrammetry & Remote Sensing, 2004, pp. 239-258, vol. 58.

Creelman, Robert A., et al., "A scanning electron microscope method for automated, quantitative analysis of mineral matter in coal," International Journal of Coal Geology, 1996, pp. 249-269, vol. 30.

Unknown, "Energy-dispersive X-ray spectroscopy," Wikepedia, http://en.wikipedia.org/wiki/Engergy_Dispersive_Spectroscopy, obtained Jul. 29, 2013, 3 pages.

Fandrich, Rolf, et al., "Modern SEM-based mineral liberation analysis," Int. J. Miner. Process., 2007, pp. 310-320, vol. 84.

Furse, J.E., "Kinematic design of fine mechanisms in instruments," J. Phys. E: Sci. Instrum, 1981, pp. 264-272, vol. 14.

Ghassemian, Hassan, et al., "Object-Oriented Feature Extraction Method for Image Data Compaction," IEEE Control Systems Magazine, Jun. 1998, pp. 42-48.

Gottlieb, P., et al., "The Automatic Identification and Quantification of Silver Minerals," XVIII International Mineral Processing Congress, May 23-28, 1993, pp. 475-481.

Gottlieb, P. et al., "Using Quantitative Electron Microscopy for Process Mineralogy Applications," JOM, Apr. 2000, pp. 24-25.

Gu, Ying, "Automated Scanning Electron Microscope Based Mineral Liberation Analysis, an Introduction to JKMRC/FEI Mineral Liberation Analyser," Journal of Mineral & Materials Characterization & Engineering, 2003, pp. 33-41, vol. 2, No. 1.

Hale, Layton C., et al., "Optimal design techniques for kinematic couplings," Journal of the International Societies for Precision Engineering and Nanotechnology, 2001, pp. 114-127, vol. 25.

Hazel, Geoffrey G., "Object-level Processing of Spectral Imagery for Detection of Targets and Changes Using Spatial-Spectral-Temporal Techniques," Proceeding of the SPIE, 2001, pp. 380-390, vol. 4381.

Jana, Dipayan, "Sample Preparation Techniques in Petrographic Examinations of Construction Materials: A State-of the-Art Review," Proceedings of the twenty-eighth Conference on Cement Microscopy, Apr. 30-May 4, 2006, 48 pages.

Lapicki, Adam, et al., "Kinematic sample mounting system for accurate positioning of transferrable samples," J. Vac. Sci. Technol. A, Sep./Oct. 2000, pp. 2603-2605, vol. 18 No. 5.

Meyer, K., et al., "Qualitative and quantitative mixture analysis by library search: infrared analysis of mixtures of carbohydrates," Analytica Chimica Acta, 1993, pp. 161-171, vol. 281.

* cited by examiner

PROCESS FOR PERFORMING AUTOMATED MINERALOGY

TECHNICAL FIELD OF THE INVENTION

The present invention relates to the field of automated mineralogy, and in particular to the use of charged particle beams in automated mineralogy systems.

BACKGROUND OF THE INVENTION

Figure 1:
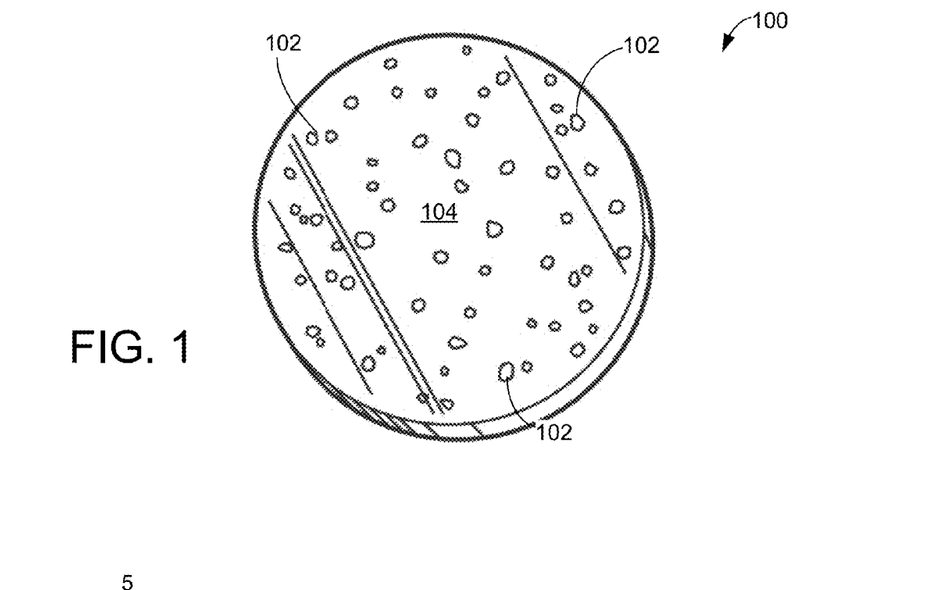
FIG. 1 shows a typical sample plug 100 for viewing in an EDS analysis system.

Mineral analysis systems, such as the QEMSCAN and MLA available from FEI Company, Hillsboro, Oreg., have been used for many years to analyze mineral samples. To determine the type and relative quantity of minerals present in a mine, a sample in the form of small granules, is fixed in epoxy and placed in a vacuum chamber. An electron beam is directed toward a sample and, in a process called "energy dispersive x-ray spectroscopy" or "EDS," the energies of x-rays coming from the sample in response to the electron beam are measured and plotted in a histogram to form a spectrum. The measured spectrum can be compared to the known spectra of various elements to determine which elements and minerals are present, and in what proportion. FIG. 1 shows a typical sample 100 having granules 102 embedded in epoxy.

Figure 2:
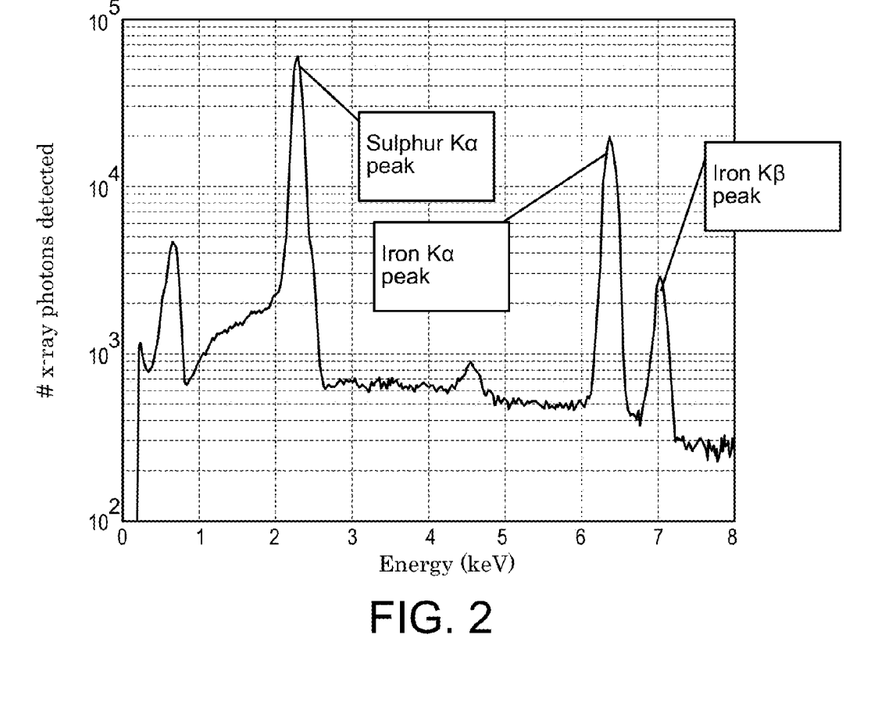
FIG. 2 shows an exemplary EDS x-ray spectrum of pyrite, which includes iron and sulfur.

It takes considerable time to accumulate an x-ray spectrum. When an electron in the primary beam impacts the sample, the electron loses energy by a variety of mechanisms. One energy loss mechanism includes transferring the electron energy to an inner shell electron, which can be ejected from the atom as a result. An outer shell electron will then fall into the inner shell, and a characteristic x-ray may be emitted. The energy of the characteristic x-ray is determined by the difference in energies between the inner shell and the outer shell. Because the energies of the shells are characteristic of the element, the energy of the x-ray is also characteristic of the material from which it is emitted. When the number of x-rays at different energies is plotted on a graph, one obtains a characteristic spectrum, such as the spectrum of pyrite shown in FIG. 2. The peaks are named for the corresponding original and final shell of the electron that originated the x-ray. FIG. 2 shows the sulfur Kα peak, the iron Kα peak and the iron Kβ peaks.

Other emissions besides characteristic x-rays are detectable when an electron beam impacts a sample surface. Emitted background or bremsstrahlung radiation x-rays are spread over a wide range of frequencies and can obscure characteristic x-ray peaks. Secondary electrons, Auger electrons, elastically and inelastically forward or back scattered electrons, and light can be emitted from the surface upon impact of a primary electron beam and can be used to form an image of the surface or to determine other properties of the surface. Backscattered electrons are typically detected by a solid state detector in which each backscattered electron is amplified as it creates many electron-hole pairs in a semiconductor detector. The backscattered electron detector signal is used to form an image as the beam is scanned, with the brightness of each image point determined by the number of backscattered electrons detected at the corresponding point on the sample as the primary beam moves across the sample.

Backscattering of electrons depends on the atomic number of the elements in the surface and upon the geometric relationship between the surface, the primary beam, and the detector. Obtaining a backscattered electron image requires collecting only a sufficient number of electrons at each point to produce a reasonable contrast between points having different properties and therefore is significantly quicker than obtaining a sufficient number of x-rays to compile a complete spectrum at each point. Also, the probability of an electron being backscattered is greater than the probability of the electron causing the emission of a characteristic x-ray of a particular frequency. Obtaining a backscattered electron image typically takes less time than acquiring sufficient x-rays to obtain an analyzable spectrum at a single dwell point.

In one mode of operating the MLA system, an image is first acquired using a backscattered electron detector, and the image is then processed to identify regions that appear from the contrast to have the same elemental composition. The beam is then positioned at the centroid of each identified region for a longer dwell time to collect an x-ray spectrum representative of the region.

Figure 3:
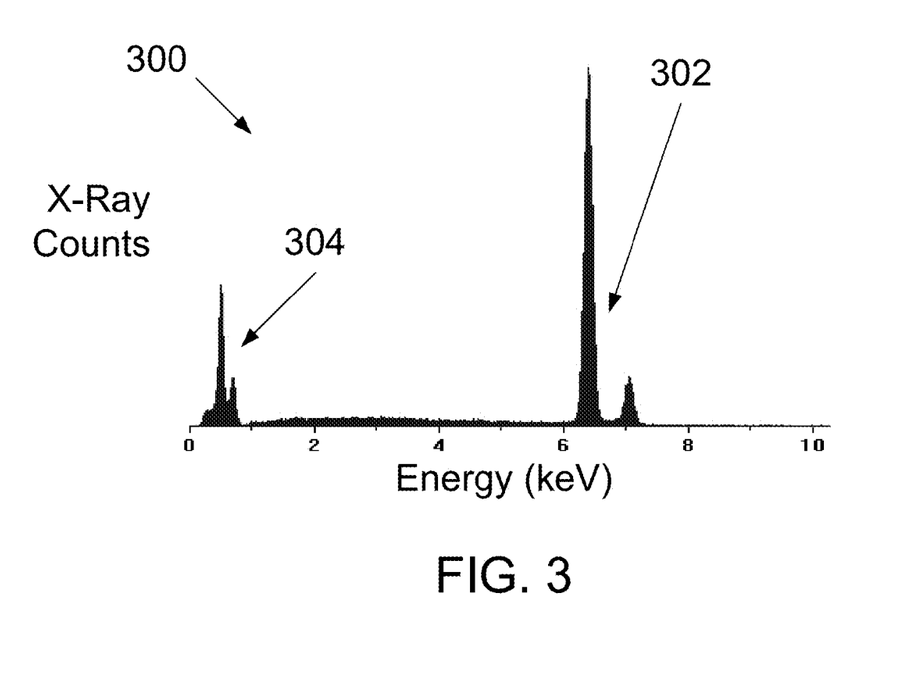
FIG. 3 shows an exemplary EDS x-ray spectrum 300 of magnetite ($Fe_3O_4$)
Figure 4:
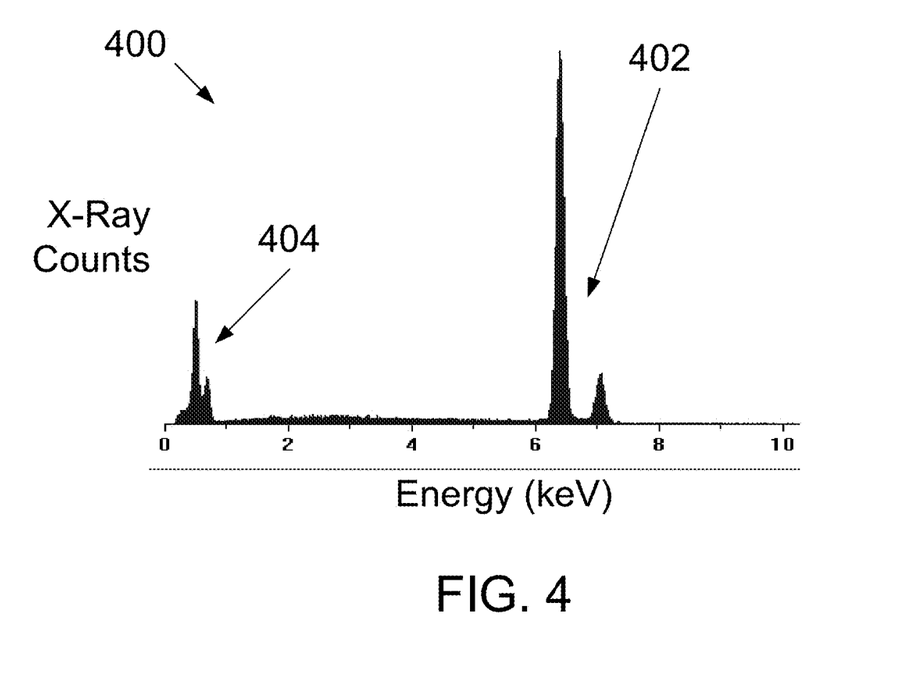
FIG. 4 shows an exemplary EDS x-ray spectrum 400 of hematite ($Fe_2O_3$)

When performing automated mineralogy on difficult samples using x-ray and back-scattered electron (BSE) information, BSE accuracy and repeatability are critical to differentiating minerals that have similar chemical formulas. For example, when analyzing iron ore it is important to accurately detect and differentiate between hematite ($Fe_2O_3$) and magnetite ($Fe_3O_4$). Although magnetite and hematite can be easily distinguished qualitatively using optical microscopy, quantitative characterization by automated scanning electron microscopy/energy dispersive x-ray spectroscopy (SEM-EDS), such as MLA, is challenging because hematite and magnetite are similar in their chemical composition and BSE brightness. The x-ray spectra for these minerals are nearly identical when collected on standard silicon drift detectors (SDD) with energy ranges of 20 eV at low x-ray counts. FIG. 3 shows an exemplary EDS x-ray spectrum 300 of magnetite ($Fe_3O_4$). FIG. 4 shows an exemplary EDS x-ray spectrum 400 of hematite ($Fe_2O_3$). A comparison of magnetite spectrum 300 and hematite spectrum 400 shows that the two spectra are very similar. Iron characteristic 102 and iron characteristic 202 are nearly identical. Oxygen characteristic 104 and oxygen characteristic 204 are also nearly identical. This similarity makes differentiating hematite and magnetite difficult for automated mineralogy applications. What is needed in the art is an improved method for automatically differentiating between minerals that have similar chemical formulas.

SUMMARY OF THE INVENTION

An object of the invention is to provide an improved method and apparatus for identifying unknown compounds in a sample material. Embodiments of the present invention are directed to a method for determining the mineral content of a sample using an electron microscope. The method includes directing an electron beam toward an area of interest of a sample, the area of interest comprising an unknown composition of minerals. The working distance between the backscattered electron detector of the microscope and the area of interest of the sample is determined. Compensation is made for the difference between the working distance and a predetermined working distance in which the predetermined working distance being the working distance that provides desired grayscale values for detected backscattered electrons. One way of compensating for working distance variation is to used an autofocus feature of the microscope to adjust the working distance. Backscattered electrons from the area of interest of the sample are then detected.

Other embodiments of the present invention are directed to a system for determining the mineral content of a sample using an electron microscope. The system includes a scanning electron microscope, one or more energy dispersive x-ray detectors, one or more backscatter electron detectors, and a system controller. The system controller includes a computer processor and a non-transitory computer-readable medium. The non-transitory computer-readable medium is encoded with computer instructions that, when executed by the computer processor, cause the system controller to direct an electron beam toward an area of interest of a sample, the area of interest comprising an unknown composition of minerals. The working distance between the backscattered electron detector of the microscope and the area of interest of the sample is determined. Compensation is made for the difference between the working distance and a predetermined working distance in which the predetermined working distance being the working distance that provides desired grayscale values for detected backscattered electrons. One way of compensating for working distance variation is to used an autofocus feature of the microscope to adjust the working distance. Backscattered electrons from the area of interest of the sample are then detected.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Embodiments of the present invention include a method for automatically configuring a scanning electron microscope (SEM)

In the MLA approach, mineral phases are first distinguished by their BSE grayscale levels during an on-line segmentation operation and then by their energy dispersive x-ray (EDX) spectrum. Minerals associated with a similar BSE values are segmented into a single phase. The results of a BSE mineral analysis determines the mineral phases and boundaries in a sample. This method of image segmentation allows BSE detectors to outline the regions of varying compounds in a sample which provides an easy means of separating the compounds and determining the overall content of a sample.

Figure 8:
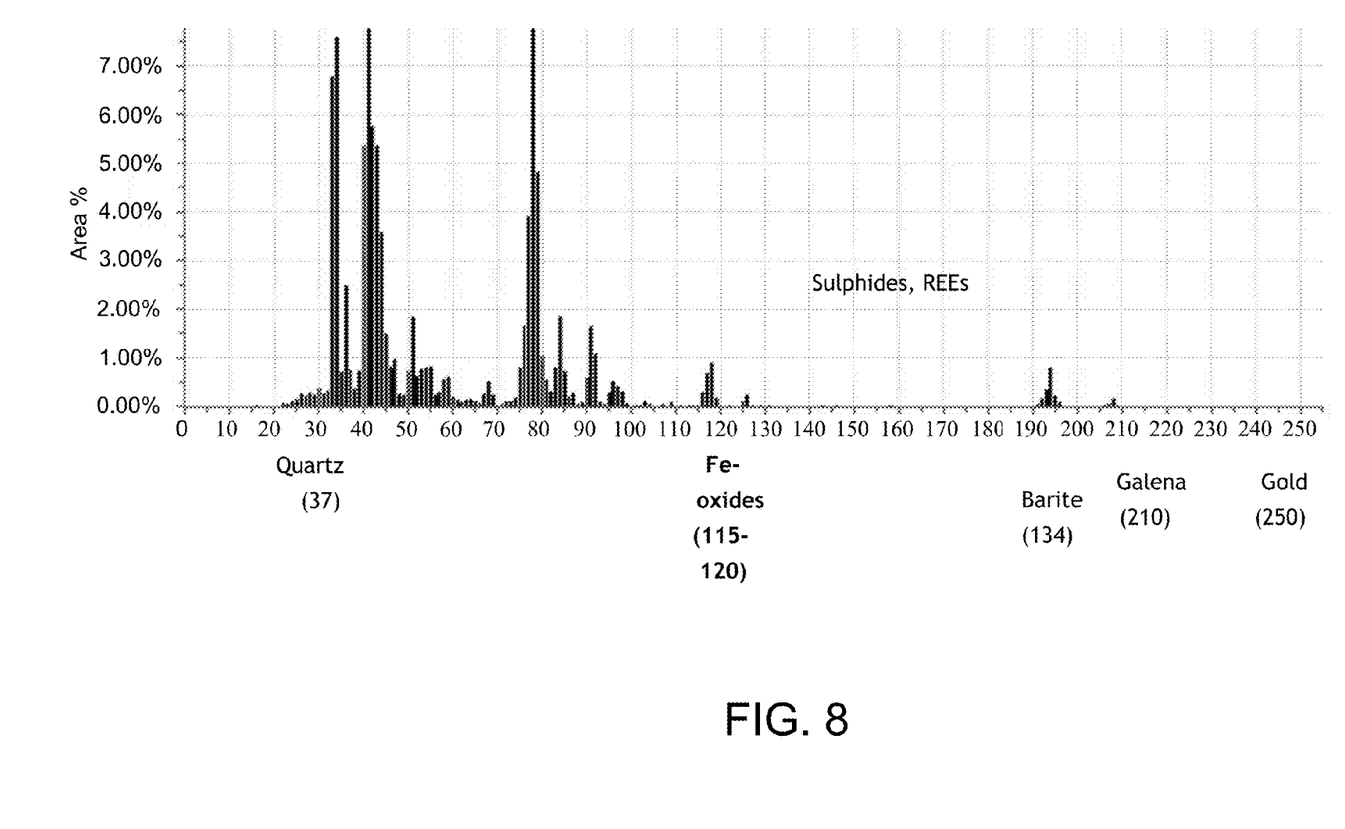
FIG. 8 shows a segmented BSE histogram reflecting standard BSE calibration.

FIG. 8 shows a segmented BSE histogram reflecting standard BSE calibration. Standard BSE calibration is set to that the mounting media (resin) is kept at backscatter brightness values below 15, and gold at value of 250. This setting covers the BSE range of all common minerals. Iron oxides typically range from 115 to 120 BSE grayscale levels. Discriminating between magnetite ($Fe_3O_4$) and hematite ($Fe_2O_3$) is difficult because both minerals appear within the narrow band of about four or five BSE grayscale levels between 115 and 120. Enhanced or stretched BSE calibration helps discriminate between the iron oxides.

Figure 9:
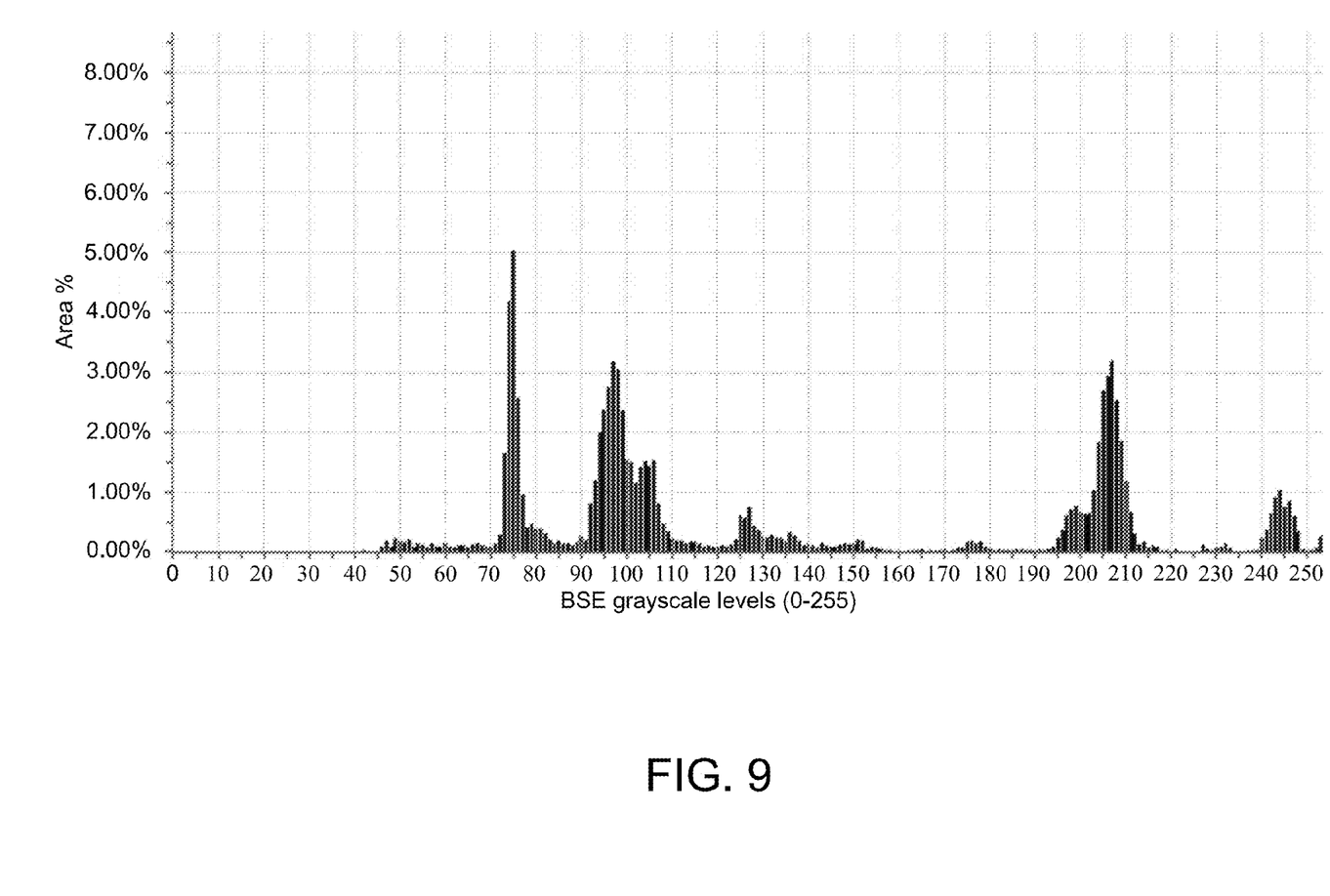
FIG. 9 shows a segmented BSE histogram reflecting enhanced or stretched BSE calibration.

FIG. 9 shows a segmented BSE histogram reflecting enhanced or stretched BSE calibration. When the contrast and brightness is increased to extend the mounting media to backscatter brightness close to 0, and chalcopyrite to 250, a bimodal peak for iron oxides emerges, ranging from 195 to 215. The bimodal peak can be separated into its two modes representing hematite (200) and magnetite (208).

For a given set of beam sample current, contrast, and brightness settings, BSE grayscale values are most impacted by changes to the distance between the sample surface and the BSE detector (the "working distance"). Therefore, to obtain the bimodal peak shown in FIG. 9, the working distance must be consistently maintained across measurements. Embodiments of the present invention utilize the "Auto Focus" feature of the SEM at each sample block to determine the focal depth and hence the current physical working distance between the surface of the sample and the BSE detector and adjusts the Z axis to bring the sample to a configured physical working distance and sets the focal depth to that same distance. Exemplary autofocus systems for electron microscopes are described, for example, in U.S. Pat. No. 5,084,618. By using autofocus to determine and adjust working distance the physical working distance is kept consistent across measurements. In the prior art, autofocus is used to keep an electron microscope image in focus. In embodiments of the present invention, autofocus is used to keep the working distance within an acceptable range. That is, if the working distance is not within an acceptable range, then the sample is moved so that it the electron microscope image is no longer in focus, but the working distance is brought within the acceptable range. The image can be brought back into focus after the working distance has been brought within the acceptable range.

In alternative embodiments, other means of determining the working distance may be used, such as a laser interferometer or a capacitive sensor. In other alternative embodiments, the effects of physical working distance variations are modeled to resultant BSE level and autofocus or other means is used to determine the current physical working distance then calculate a BSE adjustment. This embodiment is useful for systems with no Z axis adjustment capability.

For example, a sample holder may have fourteen or more "hockey puck" style samples. The center of each sample is measured to determine how high the sample is and determine the working distance between the surface of the sample and the BSE detector. In a six-inch stage, these measurements can differ by 500 micrometers or more between samples. Since only 50 micrometers of working distance or focal distance can affect the results of a BSE analysis by one grayness level, it becomes very important to maintain a constant working distance between the sample surface and the backscatter electron detector. With the measurements of the samples being potentially off by 500 micrometers or more due to imperfections in the samples, the auto focus feature is seen to be critical to the device and method disclosed. The auto focus feature will determine the precise height, on the z-axis, that every sample point will have, and adjust the height of the stage or sample to ensure a consistent working distance and focal distance.

Figure 5:
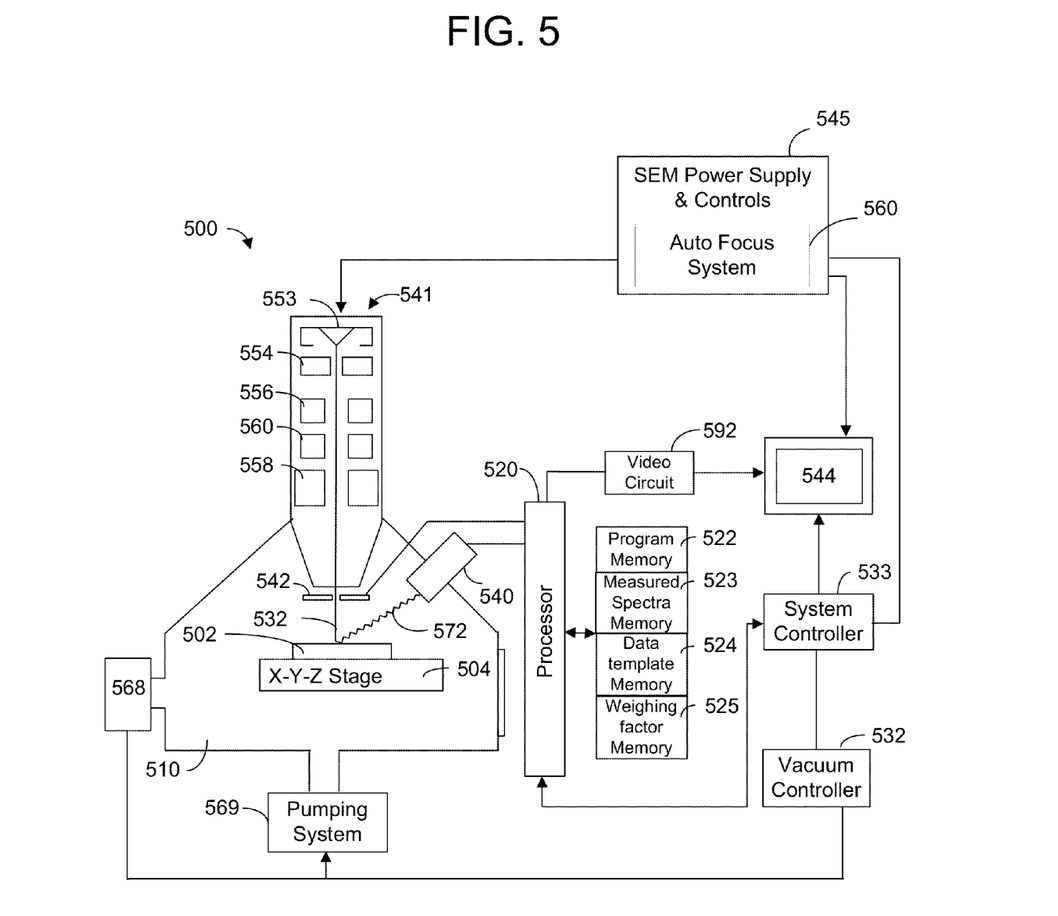
FIG. 5 shows a scanning electron beam system 500 with an x-ray detector 540 and a backscatter electron detector 542 suitable for practicing embodiments of the present invention.

FIG. 5 shows a scanning electron beam system 500 with an x-ray detector 540 and a backscatter electron detector 542 suitable for practicing embodiments of the present invention. A scanning electron microscope 541, along with power supply and control unit 545, is provided with system 500. An electron beam 532 is emitted from a cathode 553 by applying voltage between cathode 553 and an anode 554. Electron beam 532 is focused to a fine spot by means of a condensing lens 556 and an objective lens 558. Electron beam 532 is scanned two-dimensionally on the specimen by means of a deflection coil 560. Operation of condensing lens 556, objective lens 558, and deflection coil 560 is controlled by power supply and control unit 545. Scanning electron beam system 500 also includes auto focus system 560. Auto focus system 560 determines the focal depth of electron beam 532 and adjusts the lenses and deflection coil to bring the electron beam into the desired focus.

A system controller 533 controls the operations of the various parts of scanning electron beam system 500. The vacuum chamber 510 is evacuated with ion pump 568 and mechanical pumping system 569 under the control of vacuum controller 532.

Electron beam 532 can be focused onto sample 502, which is on movable X-Y stage 504 within lower vacuum chamber 510. When the electrons in the electron beam strike sample 502, the sample gives off x-rays whose energy correlated to the elements in the sample. X-rays 572 having energy inherent to the elemental composition of the sample are produced in the vicinity of the electron beam incident region. Emitted x-rays are collected by x-ray detector 540, preferably an energy dispersive detector of the silicon drift detector type, although other types of detectors could be employed, which generates a signal having an amplitude proportional to the energy of the detected x-ray. Backscattered electrons are detected by backscatter electron detector 542, preferably a segmented BSE detector.

Output from detector 540 is amplified and sorted by the processor 520, which counts and sorts the total number of X-rays detected during a specified period of time, at a selected energy and energy resolution, and a channel width (energy range) of preferably between 10-20 eV per channel. Processor 520 can comprise a computer processor; operator interface means (such as a keyboard or computer mouse); program memory 522 for storing data and executable instructions; interface means for data input and output, executable software instructions embodied in executable computer program code; and display 544 for displaying the results of a multivariate spectral analysis by way of video circuit 592.

Processor 520 can be a part of a standard laboratory personal computer, and is typically coupled to at least some form of computer-readable media. Computer-readable media, which include both volatile and nonvolatile media, removable and non-removable media, may be any available medium that can be accessed by processor 520. By way of example and not limitation, computer-readable media comprise computer storage media and communication media. Computer storage media include volatile and nonvolatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 520.

Program memory 522 can include computer storage media in the form of removable and/or non-removable, volatile and/or nonvolatile memory and can provide storage of computer-readable instructions, data structures, program modules and other data. Generally, the processor 520 is programmed by means of instructions stored at different times in the various computer-readable storage media of the computer. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described below in conjunction with a microprocessor or other data processor. The invention also includes the computer itself when programmed according to the methods and techniques described herein.

An x-ray spectrum obtained as described above can be stored in a portion of memory 522, such as the measured spectra memory portion 523. Data template memory portion 524 stores data templates, such as known spectra of elements or, in some embodiments, known diffraction patterns of materials. Weighing Factor Memory portion 525 stores weighting factor for each of the data templates, the weighting factors combining with the data templates to produce a calculated spectrum approximating the measured spectrum. The weighting factors correlated to the abundance in the sample of the element corresponding to the data template. Processor 520 uses the methods described above to minimize an error value which represents the different between the measured pattern and the combination of the data templates and weighting factors.

Figure 6:
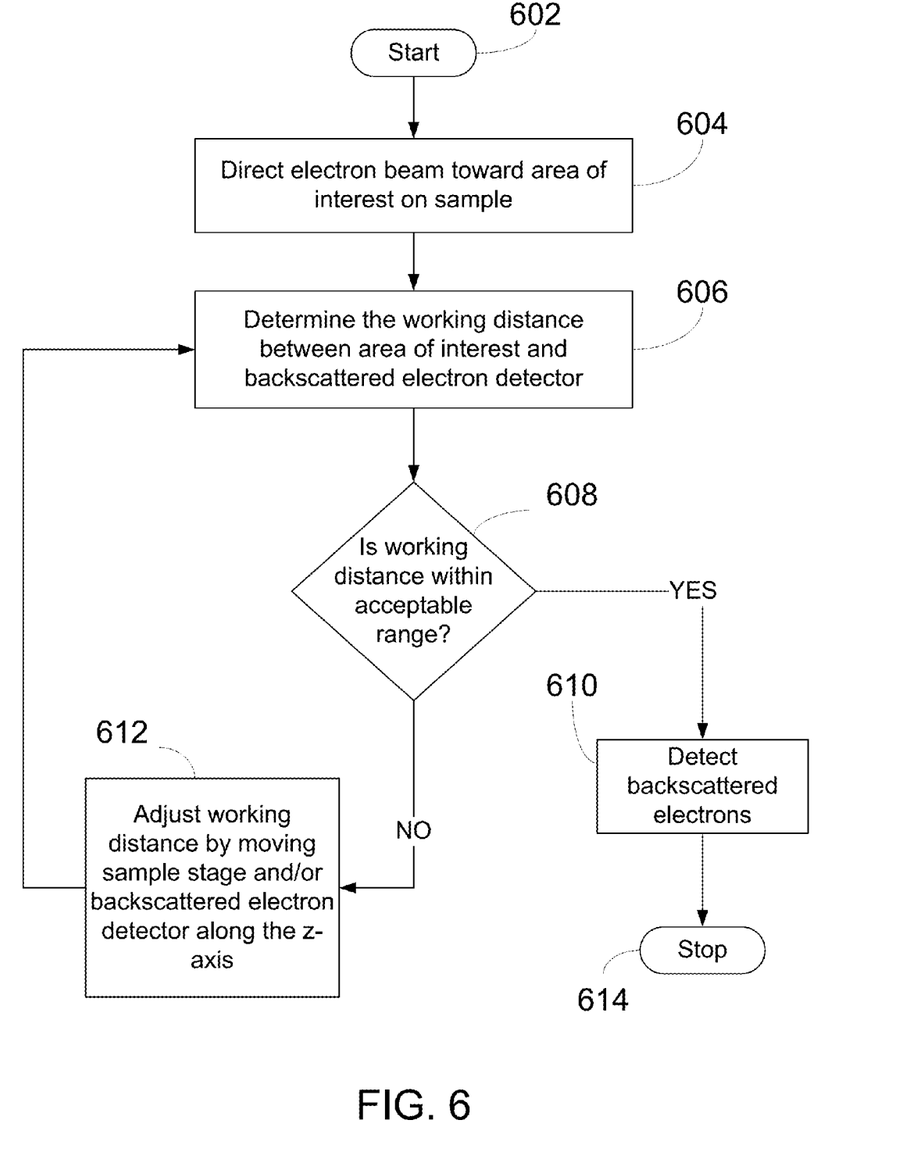
FIG. 6 shows a flowchart of a method for operating an automated mineralogy system in accordance with one or more embodiments of the present invention.

FIG. 6 shows a flowchart of a method for operating an automated mineralogy system in accordance with one or more embodiments of the present invention. The method shown in FIG. 6 is particularly suited for systems that have a means for adjusting the working distance between sample 502 and backscatter electron detector 542. For example, sample stage 504 can be adjustable in the z-axis to translate sample stage 504 closer to or farther from backscatter electron detector 542. The method begins at start block 602. Electron beam 532 is directed toward an area of interest on the sample surface (step 604). System controller 533 can automatically configure SEM 541 by setting and measuring the sample beam current of electron beam 532 and automatically setting contrast and brightness levels using two standard materials. For example, when analyzing iron ore, chalcopyrite and quartz can be used as standard materials.

Auto focus system 560 is then used to determine the working distance between sample 502 and backscatter electron detector 542 (step 606). The system then determines whether the working distance is within a predetermined acceptable range (step 608). The predetermined acceptable range is the narrow range of working distances for which, given set of beam sample current, contrast, and brightness settings, produce the BSE grayscale values best discriminate between the elements or compounds that are being identified. If the working distance is within the predetermined acceptable range, then the system proceeds with backscatter electron detection (step 610). If the working distance is not within the predetermined acceptable range, then the system adjusts the working distance between sample 502 and backscatter electron detector 542 so that the working distance is within the predetermined acceptable range (step 612). In one embodiment, sample stage 504 is translated in the z-axis to move sample 502 closer to or farther from the backscatter electron detector 542. If the working distance is smaller than the predetermined acceptable range, then sample stage 504 is translated in the z-axis away from the backscatter electron detector 542 so the working distance is increased until the working distance is within the predetermined acceptable range. If the working distance is larger than the predetermined acceptable range, then sample stage 504 is translated in the z-axis toward the backscatter electron detector 542 so the working distance is decreased until the working distance is within the predetermined acceptable range. In alternative embodiments, backscatter electron detector 542 is translated in the z-axis to bring the working distance within the predetermined acceptable range. Once the working distance is within the predetermined acceptable range, then the system proceeds with backscatter electron detection (step 610). The process ends at stop block 614.

Figure 7:
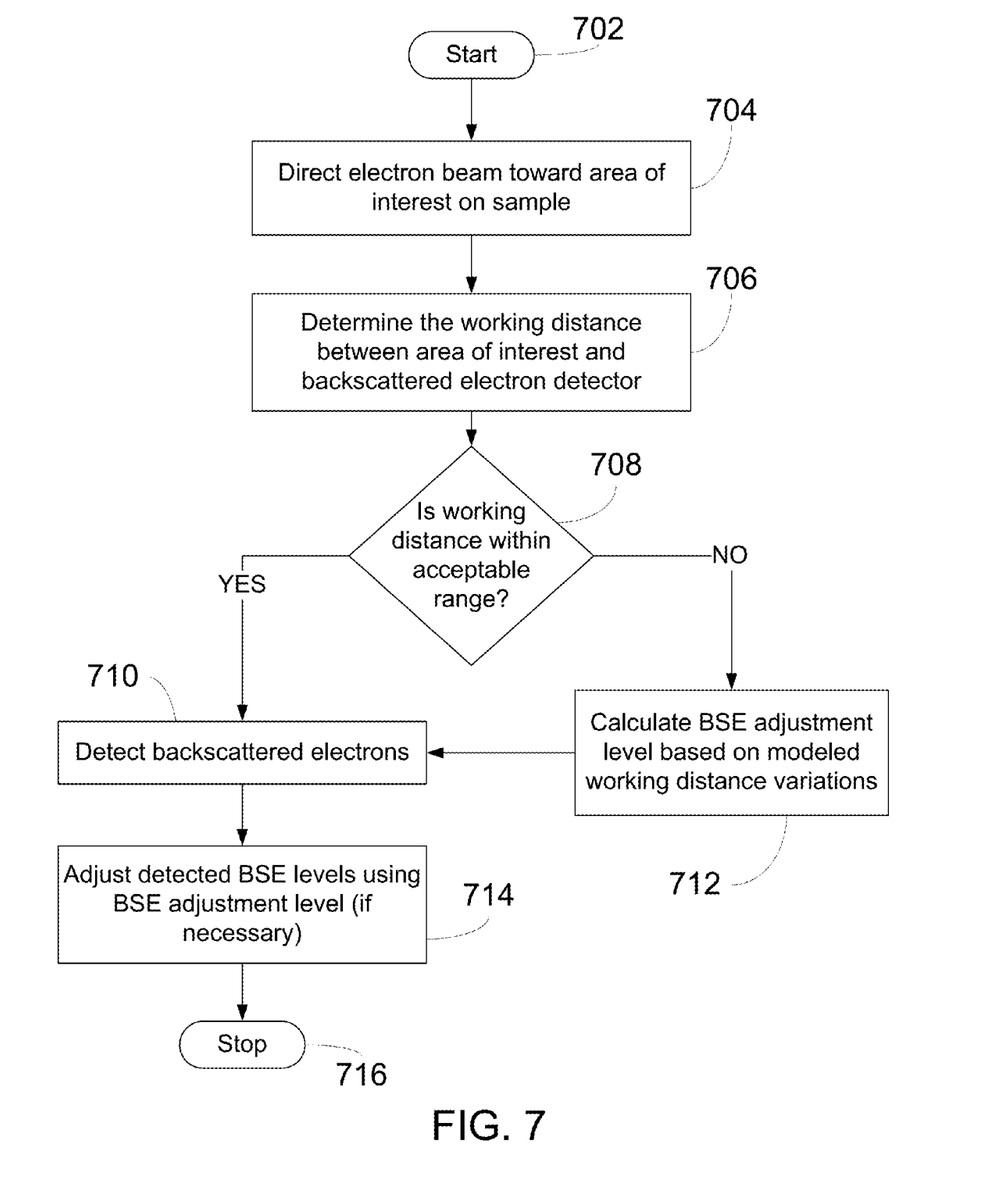
FIG. 7 shows a flowchart of an alternative method for operating an automated mineralogy system in accordance with one or more embodiments of the present invention.

FIG. 7 shows a flowchart of an alternative method for operating an automated mineralogy system in accordance with one or more embodiments of the present invention. The method shown in FIG. 7 is particularly suited for systems that do not have a means for adjusting the working distance between sample 502 and backscatter electron detector 542. For example, sample stage 504 might only translate in the x and y direction and might fixed in the z-axis and unable to translate sample stage 504 closer to or farther from backscatter electron detector 542. The method begins at start block 702. Electron beam 532 is directed toward an area of interest on the sample surface (step 704). System controller 533 can automatically configure SEM 541 by setting and measuring the sample beam current of electron beam 532 and automatically setting contrast and brightness levels using two standard materials. For example, when analyzing iron ore, chalcopyrite and quartz can be used as standard materials.

Auto focus system 560 is then used to determine the working distance between sample 502 and backscatter electron detector 542 (step 706). The system then determines whether the working distance is within a predetermined acceptable range (step 708). The predetermined acceptable range is the narrow range of working distances which produce the BSE grayscale values that best discriminate between the elements or compounds that are being identified. If the working distance is within the predetermined acceptable range, then the system proceeds with backscatter electron detection (step 710). If the working distance is not within the predetermined acceptable range, then the system calculates a BSE adjustment level based on modeled working distance variations and the measured working distance (step 712). The system proceeds with backscatter electron detection (step 710) and adjusts the detected BSE levels using the calculated BSE adjustment level (step 714). The process ends at stop block 716.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for determining mineral contents of samples using an electron microscope, said method comprising:
   directing an electron beam toward a surface of a first sample comprising an unknown composition of minerals;
   determining a first working distance, the first working distance being the distance between a backscattered electron detector of the electron microscope and the surface of the first sample, by determining a focal distance of the surface of the first sample using an auto-focus feature of the electron microscope;
   compensating for the difference between the first working distance and a predetermined working distance, the predetermined working distance being the working distance that provides desired grayscale values for detected backscattered electrons; and
   detecting backscattered electrons from the surface of the first sample.

2. The method of claim 1, further comprising:
   directing an electron beam toward a surface of a second sample comprising an unknown composition of minerals;
   determining a second working distance, the second working distance being the distance between the backscattered electron detector and surface of the second sample;
   compensating for the difference between the second working distance and the first working distance; and
   detecting backscattered electrons from the surface of the second sample.

3. The method of claim 2, in which determining the second working distance further comprises determining a focal distance of the surface of the second sample, the focal distance being determined using an auto-focus feature of the electron microscope.

4. The method of claim 1, in which compensating for the difference between the first working distance and a predetermined working distance further comprises adjusting a z-axis position of a sample stage and/or the backscattered electron detector so that there is substantially no difference between the first working distance and the predetermined working distance.

5. The method of claim 1, in which compensating for the difference between the first working distance and a predetermined working distance further comprises:
   modeling an effect of a plurality of working distance variations on detected backscattered electron grayscale levels;
   calculating a backscattered electron grayscale level adjustment based on the difference between the first working distance and the predetermined working distance; and adjusting one or more of the detected backscattered electron grayscale levels based on the calculated backscattered electron grayscale level adjustment.

6. The method of claim 2, in which compensating for the difference between the second working distance and the first working distance further comprises:
modeling an effect of a plurality of working distance variations on detected backscattered electron grayscale levels;
calculating a backscattered electron grayscale level adjustment based on the difference between the second working distance and the first working distance; and
adjusting one or more of the detected backscattered electron grayscale levels based on the calculated backscattered electron grayscale level adjustment.

7. The method of claim 1, further comprising determining the mineral composition of the first sample where the electron beam irradiates the surface of the first sample based on detected backscattered electron grayscale levels.

8. The method of claim 2, further comprising:
determining the mineral composition of the first sample where the electron beam irradiates the surface of the first sample based on detected backscattered electron grayscale levels from the first sample; and
determining the mineral composition of the second sample where the electron beam irradiates the surface of the second sample based on detected backscattered electron grayscale levels from second sample.

9. The method of claim 1, further comprising:
detecting energies of x-rays emitted in response to the electron beam; and
determining the mineral composition of the first sample where the electron beam irradiates the surface of the first sample based on detected backscattered electron grayscale levels and the detected x-ray energies.

10. A method for determining mineral contents of samples using an electron microscope, said method comprising:
directing an electron beam toward a surface of a first sample comprising an unknown composition of minerals;
determining a first focal distance of the surface of the first sample, the first focal distance being determined using an auto-focus feature of the electron microscope;
determining a first working distance based on the first focal distance, the first working distance being the distance between a backscattered electron detector of the electron microscope and the surface of the first sample;
detecting backscattered electrons from the surface of the first sample;
directing an electron beam toward a surface of a second sample comprising an unknown composition of minerals;
determining a second focal distance of the surface of the second sample, the second focal distance being determined using the auto-focus feature of the electron microscope;
determining a second working distance based on the second focal distance, the second working distance being the distance between the backscattered electron detector of the electron microscope and the surface of the second sample;
adjusting a z-axis position of a sample stage and/or the backscattered electron detector so that there is substantially no difference between the second working distance and the first working distance; and
detecting backscattered electrons from the surface of the second sample.

11. A system for determining mineral contents of samples using a scanning electron microscope, said system comprising:
a scanning electron microscope;
one or more energy dispersive x-ray detectors;
a backscattered electron detector of the scanning electron microscope;
a system controller, the system controller comprising a computer processor and a non-transitory computer-readable medium, the non-transitory computer-readable medium being encoded with computer instructions that, when executed by the computer processor, cause the system controller to perform the steps of:
directing an electron beam toward a surface of a first sample comprising an unknown composition of minerals;
determining a first working distance, the first working distance being the distance between a backscattered electron detector and the surface of the first sample, by determining a focal distance of the surface of the first sample using an auto-focus feature of the scanning electron microscope;
compensating for the difference between the first working distance and a predetermined working distance, the predetermined working distance being the working distance that provides desired grayscale values for detected backscattered electrons; and
detecting backscattered electrons from a region of the surface of the first sample.

12. The system of claim 11, further comprising computer instructions for:
directing an electron beam toward a surface of a second sample comprising an unknown composition of minerals;
determining a second working distance, the second working distance being the distance between the backscattered electron detector and the surface of the second sample;
compensating for the difference between the second working distance and the first working distance; and
detecting backscattered electrons from a region of the surface of the second sample.

13. The system of claim 12, in which the computer instructions for determining the second working distance further comprise computer instructions for determining a focal distance of the surface of the second sample, the focal distance being determined using an auto-focus feature of the scanning electron microscope.

14. The system of claim 11, in which the computer instructions for compensating for the difference between the first working distance and a predetermined working distance further comprise computer instructions for adjusting a z-axis position of a sample stage and/or the backscattered electron detector so that there is substantially no difference between the first working distance and the predetermined working distance.

15. The system of claim 11, in which the computer instructions for compensating for the difference between the first working distance and a predetermined working distance further comprises computer instructions for:
modeling an effect of a plurality of working distance variations on detected backscattered electron grayscale levels;
calculating a backscattered electron grayscale level adjustment based on the difference between the first working distance and the predetermined working distance; and adjusting one or more of the detected backscattered electron grayscale levels based on the calculated backscattered electron grayscale level adjustment.

16. The system of claim 12, in which the computer instructions for compensating for the difference between the second working distance and the first working distance further comprises computer instructions for:
    modeling an effect of a plurality of working distance variations on detected backscattered electron grayscale levels;
    calculating a backscattered electron grayscale level adjustment based on the difference between the second working distance and the first working distance; and
    adjusting one or more of the detected backscattered electron grayscale levels based on the calculated backscattered electron grayscale level adjustment.

17. The system of claim 11, further comprising computer instructions for determining the mineral composition of the first sample at the region of the surface of the first sample based on the detected backscattered electrons.

18. The system of claim 12, further comprising computer instructions for:
    determining a mineral composition of the first sample at the region of the surface of the first sample based on the detected backscattered electrons from the first area of interest; and
    determining a mineral composition of the second sample at the region of the surface of the second sample based on the detected backscattered electrons from second area of interest.

19. The system of claim 11, further comprising computer instructions for:
    detecting energies of x-rays emitted in response to the electron beam; and
    determining the mineral composition of the first sample at the region of the surface of the first sample based on detected backscattered electron grayscale levels and the detected x-ray energies.

* * * * *